United States Patent [19]

Leroy et al.

[11] Patent Number: 5,100,398
[45] Date of Patent: Mar. 31, 1992

[54] DISPOSABLE DIAPER WITH CROTCH ELASTICS AND LATERAL SEALING COATING

[75] Inventors: Andre Leroy, Mouveaux; Yves Villez, Linselles, both of France

[73] Assignee: Peaudouce, Linselles, France

[21] Appl. No.: 225,708

[22] Filed: Jul. 27, 1988

[30] Foreign Application Priority Data

Jul. 30, 1987 [FR] France .................. 87 10834

[51] Int. Cl.$^5$ .................... A61F 13/16
[52] U.S. Cl. .................... 604/385.1; 604/370; 604/382
[58] Field of Search ............. 604/385.2, 385.1, 370, 604/381, 382

[56] References Cited

U.S. PATENT DOCUMENTS

| 3,386,442 | 6/1968 | Sabee . | |
|---|---|---|---|
| 3,520,303 | 7/1970 | Endres . | |
| 3,604,422 | 9/1971 | Sabee . | |
| 3,799,167 | 3/1974 | Miller et al. . | |
| 3,860,003 | 1/1975 | Buell | 604/385.2 |
| 4,081,301 | 3/1978 | Buell | 156/164 |
| 4,090,515 | 5/1978 | Karami | 604/382 X |
| 4,353,762 | 10/1982 | Bouda | 156/164 |
| 4,425,127 | 1/1984 | Suzuki et al. | 604/366 |
| 4,578,071 | 3/1986 | Buell | 604/379 |
| 4,585,447 | 4/1986 | Karami | 604/385.2 |
| 4,585,449 | 4/1986 | Karami | 604/378 |
| 4,610,685 | 9/1986 | Raley | 604/366 |
| 4,643,728 | 2/1987 | Karami | 604/385.2 |
| 4,654,039 | 3/1987 | Brandt et al. | 604/368 |
| 4,661,102 | 4/1987 | Shikata et al. | 604/385.2 |
| 4,687,477 | 7/1987 | Suzuki et al. | 604/385.2 |
| 4,804,379 | 2/1989 | Toth et al. | 604/378 |
| 4,850,989 | 7/1989 | Villez | 604/385.2 |

FOREIGN PATENT DOCUMENTS 0059014 1/1982 European Pat. Off. .
0113976 7/1984 European Pat. Off. .
0196654 10/1986 European Pat. Off. .

Primary Examiner—C. Fred Rosenbaum
Assistant Examiner—Mark O. Polutta
Attorney, Agent, or Firm—Owen, Wickersham & Erickson

[57] ABSTRACT

Disposable diaper for incontinent children or adults, of the type comprising an outer enclosure (1) impervious to liquids, an absorbent pad (11) fastened inside the impervious enclosure, set back in relation to the outer edges of the impervious enclosure, so as to leave a lateral border (12) remaining on each side of the pad, an internal permeable sheet (17) overlapping the inner face of the impervious enclosure and the absorbent pad, at least one lateral elastic member (8) fastened by adhesive bonding in the stretched state in a median transverse region of each lateral border of the impervious enclosure and two bands (16) of flexible sheet which are fastened to the impervious enclosure so that each band encloses a lateral elastic member (8) in an insulating sheath extending over the whole length of the impervious enclosure, characterized in that the lateral regions of the internal permeable sheet are covered over with a coating (19) of a sealing material which is liquid at high temperature and which, after cooling, forms a barrier against the propagation of liquids, within the thickness of the said permeable sheet (17), the said coating being produced as far as the parts of the permeable sheet which overlap the lateral borders of the absorbent pad and over the whole length of the diaper.

18 Claims, 2 Drawing Sheets

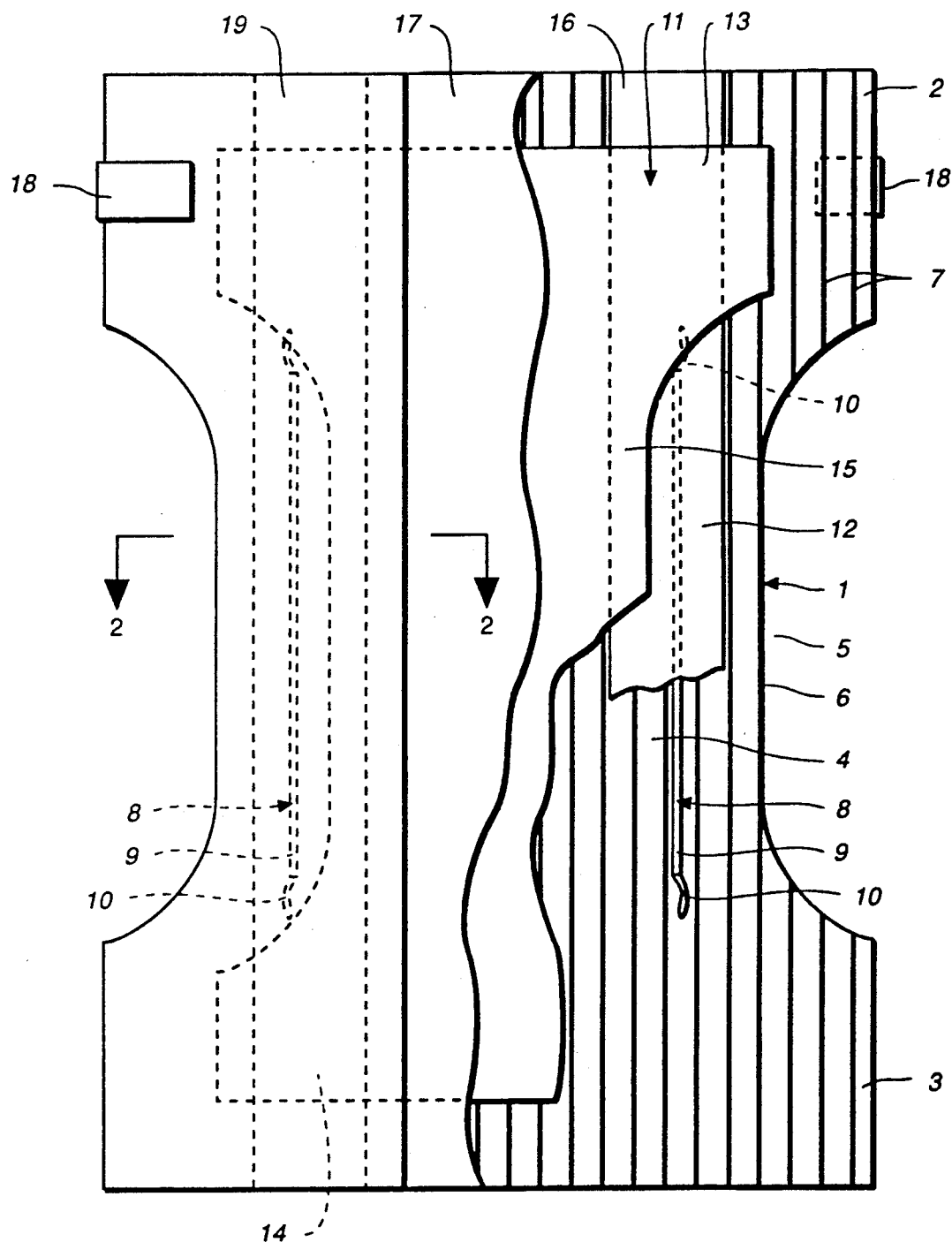
FIG._1

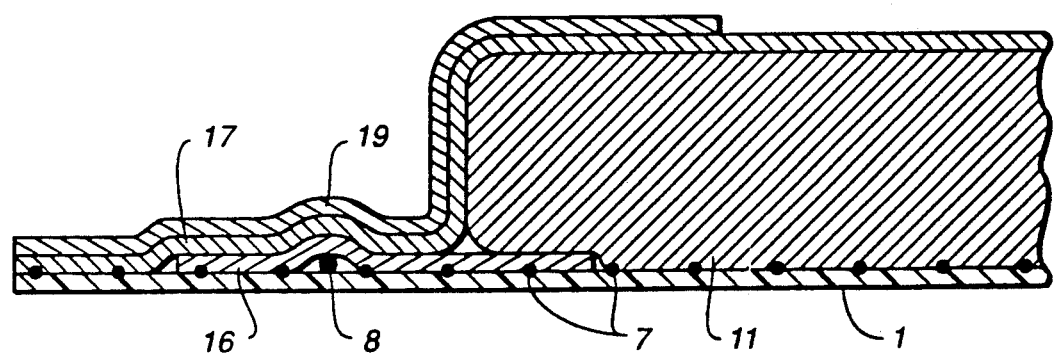
FIG._2
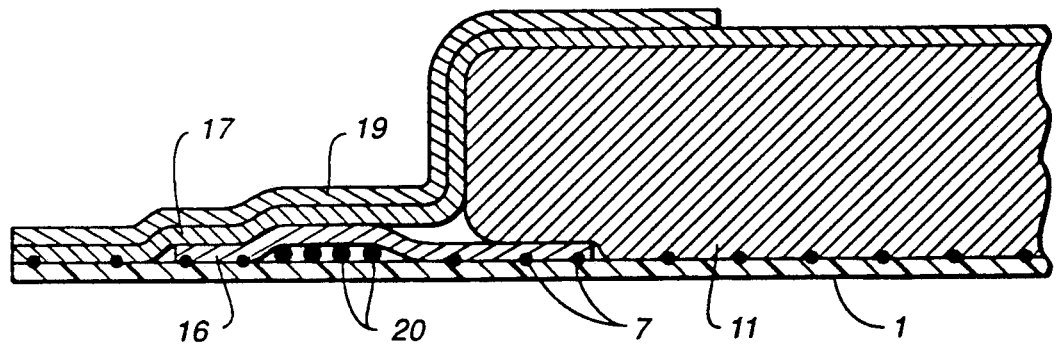
FIG._3
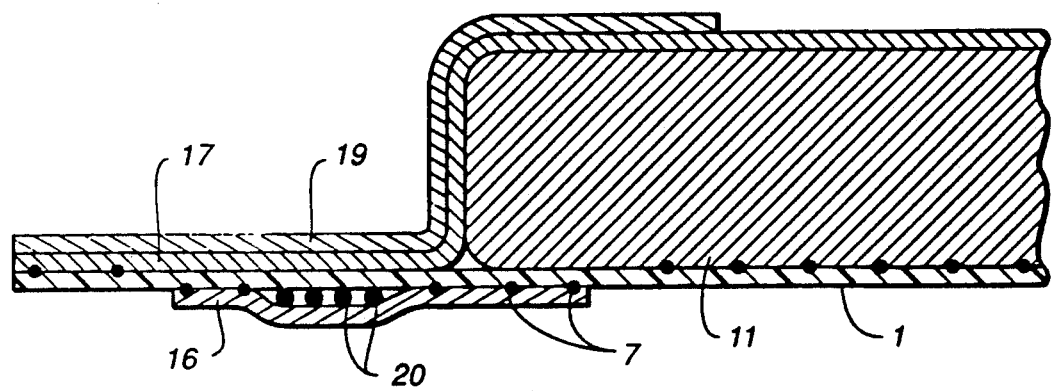
FIG._4

DISPOSABLE DIAPER WITH CROTCH ELASTICS AND LATERAL SEALING COATING

The present invention relates to disposable diapers for incontinent children or adults. The diapers of the type of the invention comprise an outer enclosure impervious to liquids, which may be advantageously made from an impervious thin flexible sheet, for example of polyethylene. An absorbent pad is fastened to the inside of the impervious enclosure, set back in relation to the outermost edges of the impervious enclosure so as to leave a lateral border remaining on each side of the absorbent pad. The absorbent pad may advantageously comprise defibred cellulose pulp, generally called "fluff" in the art, as well as, optionally, particles or grains of superabsorbent material, that is to say of polymeric material capable of absorbing several times its volume of liquid. A permeable inner sheet generally overlaps the inner face of the impervious enclosure and the absorbent pad. This permeable sheet is usually a nonwoven voile capable of allowing liquids to pass through so that they can enter the absorbent pad. The absorbent pad is fastened, advantageously by adhesive bonding, over the majority of its surface, for example by means of lengthwise lines of adhesive coating. The permeable sheet is also fastened by adhesive bonding, for example by means of lengthwise lines of adhesive to the upper surface of the absorbent pad and to the lateral border regions and to the front and rear regions of the impervious enclosure which overlaps the absorbent pad. At least one lateral elastic member is fastened by adhesive bonding in the stretched state in a median transverse region of each lateral border of the impervious enclosure Two bands of flexible sheet are fastened to the impervious enclosure that each band encloses a lateral elastic member in an insulating sheath extending over the whole length of the impervious enclosure.

When such individual diapers are manufactured, the elastic members are applied in the stretched state and continuously on the flexible sheet intended to form the impervious enclosure of the diapers. These elastic members are coated with adhesive in a noncontinuous manner so that only their adhesive-coated sections adhere to the impervious sheet. At the end of manufacture, a transverse cut of the manufactured strip is made, this cut being made between the successive absorbent pads so as to define the individual diapers. During this transverse cut, the sections of the elastic members which are not coated with adhesive retract freely inside the insulating sheaths formed by the bands of flexible sheet. The existence of these insulating sheaths makes it possible to prevent the outward escape of the liquids absorbed by the pad of the diaper, at the location of the transverse edges of the diaper. Furthermore, by virtue of the existence of these insulating sheaths, the material of which the absorbent pad is made and, in particular, optional particles of superabsorbent which are arranged inside the diaper on the inner face of the impervious enclosure cannot enter the sheaths thus defined and escape outwards because these sheaths or tunnels are open only at the transverse outermost edges of the diaper.

In the usual diapers known hitherto, attempts have been made to solve the problem of the outward migration of the liquids present in the absorbent pad. Thus, provision has already been made for arranging, in the vicinity of the front and rear transverse borders of the diaper, members forming a barrier and capable of preventing the rise of liquids from the absorbent pad towards the belt region of the diaper by retarding the migration of the liquids within the lateral regions of the diaper by means of the permeable sheet which overlaps the whole of the internal surface of the diaper. Thus, U.S. Pat. No. 3,520,303 (Endres), U.S. Pat. No. 3,606,422 (Sabee) and U.S. Pat. No. 3,386,442 (Sabee) describe diapers, devoid of crotch elastics, but comprising bands of plastic material overlapping the lateral borders of the absorbent pad. U.S. Pat. No. 3,799,167 (Miller) envisages treating the peripheral regions of an absorbent with a polymer emulsion which is subjected to a heat cure treatment after application. No crotch elastic is envisaged in this document.

All these previous solutions, while appearing theoretically capable of solving the problem of lateral sealing, cannot, however, be applied in the mass manufacture of disposable diapers. Moreover, they are completely inappropriate in the case of diapers comprising crotch elastics. European Patent Application EP 59,014 (Procter & Gamble), which describes a diaper with crotch elastics, has tried to solve the difficulty by making lengthwise lines of compression of the material in parallel with the elastics in order to retard the migration of the liquids. Apart from providing only a relative sealing, an embodiment of this kind does not make it possible to avoid the rise of the liquids directly via the absorbent pad.

Other solutions have been recommended to produce a kind of window with impervious edges by means of the addition of a thin sheet of plastic inside the diaper itself. Patents FR 2,181,792 (Paper Converting), FR 2,299,824 (CGT) and FR 2,522,521 (Beghin-Say) describe diapers of this type which have not been wholly satisfactory in practice. In addition, such embodiments are complicated to manufacture, given that sheet members must be added after appropriate cutting and an additional suitable adhesive bonding must be performed inside the diaper itself.

The subject of the present invention is a diaper of the type referred to in the preamble of the description, in which the outward migration of the liquids from the absorbent pad in the lateral regions is eliminated or very largely decreased, this being done without affecting the action of the elastic members which can thus continue to fulfil their function of adapting the diaper to the morphology of the user, and of improving the sealing at the leg passages. It is appropriate, in fact, to provide at the time of manufacture, means permitting the passage of lateral elastic members and not preventing the retraction of their end portions which are not coated with adhesive, during the final cutting of the individual diapers.

The disposable diaper for incontinent children or adults according to the present invention is of the type comprising an outer enclosure impervious to liquids, an absorbent pad fastened inside the impervious enclosure, set back in relation to the outermost edges of the impervious enclosure so as to leave a lateral border remaining on each side of the pad, an internal permeable sheet overlapping the inner face of the impervious enclosure and the absorbent pad, at least one lateral elastic member fastened by adhesive bonding in the stretched state in a median transverse region of each lateral border of the impervious enclosure and two bands of flexible sheet which are fastened to the impervious enclosure so that each band encloses a lateral elastic member in an insulating sheath extending over the whole length of the impervious enclosure. According to the invention, the lateral regions of the inner permeable sheet are covered over, preferably on their face directed towards the outside of the diaper, with a coating of a sealing material which is liquid at high temperature and which, after cooling in the thickness of the said sheet, forms a barrier against the propagation of liquids, the said coating being produced as far as the parts of the permeable sheet which overlap the lateral borders of the absorbent pad and over the whole length of the diaper. The "face directed towards the outside of the diaper" or outer face, means the face of the inner permeable sheet which comes into contact with the absorbent pad. The coating extends partly into the thickness of the permeable sheet without, however, passing completely through the said sheet. The inner face of the permeable sheet retains, therefore, a feel and a surface state which is soft for contact with the user's skin.

The coating preferably extends as far as the outermost lateral edges of the diaper.

In an advantageous embodiment of the invention, the bands of the insulating sheaths are fastened onto the inner face of the impervious enclosure and enclose the elastic members which are also fastened by adhesive bonding onto the inner face of the impervious enclosure. In this case, the bands are preferably made of a liquid-impervious thin sheet, for example of polyethylene.

By virtue of the existence of these bands of impervious thin sheet, there is no risk that the liquid material at high temperature which passes through the thickness of the inner permeable sheet will come into contact with the elastic members and, in particular, with their ends which are not coated with adhesive, since the elastic members are separated from the inner permeable sheet by the insulating sheath formed by the band of impermeable flexible sheet which covers them. By virtue of this arrangement, it therefore becomes possible to easily coat the outer face of the permeable sheet in its lateral regions so as to obtain a barrier action against the propagation of the liquids in the region of the leg passages, without interfering with the process of manufacture of the diaper and, in particular, without in any way impeding the retraction of the free ends, not coated with adhesive, of the lateral elastic members during the cutting which forms the individual diapers.

In another embodiment, the bands of the insulating sheaths are fastened onto the outer face of the impervious enclosure and enclose the elastic members which are also fastened by adhesive bonding onto the outer face of the impervious enclosure. In this embodiment, it is not essential for the band to be made of an impervious material and it is possible to envisage making this band of any other material such as a nonwoven. As in the preceding embodiment, the elastic members are completely insulated from the coating material which enters within the thickness of the inner permeable sheet, the insulation being this time produced by the outer impervious enclosure itself. The same advantages as in the preceding embodiment are therefore obtained.

It appears that the invention lies in the combination of the coating of the sealing material which is liquid at high temperature forming, after cooling, a barrier against the propagation of the liquids within the very thickness of the inner permeable sheet, with the bands fastened to the impervious enclosure and forming an insulating sheath extending over the whole length of the impervious enclosure, enclosing the lateral elastic members.

The structure of the lateral elastic members is not critical in itself for the present invention. Thus, elastic members each of which consists of a small band of elastic material, for example of rubber or any other material, can be employed. It is also possible to employ elastic members consisting of a plurality of individual strands placed parallel to each other, in groups if desired.

In general, and for reasons of simplifying the process of manufacture, elastic members adhesively bonded in the rectilinear state will be employed. However, it would be perfectly possible to envisage the use of curvilinear elastic members, as long as the dimensions of the insulating sheath were capable of receiving the nonrectilinear elastic members.

Throughout the description of the invention, the term "outer" is used to describe the constituent members directed outwards when the diaper is worn by the user and 'inner' the constituent members situated between the user and the impervious sheet.

The present invention will be better understood from the study of a few embodiments described by way of examples, without any limitation being implied, and illustrated by the attached drawings, in which:

FIG. 1 is a top view, with cutaway, of a diaper according to the invention, shown in the stretched state and flat, with the inner face upwards;

FIG. 2 is a partial view in section along II—II of FIG. 1, with the thicknesses of the various materials greatly exaggerated;

FIG. 3 is a view similar to FIG. 2, of an alternative form of embodiment employing elastics comprising a plurality of individual strands; and FIG. 4 is a view similar to FIGS. 2 and 3, showing another alternative form of the invention, in which the elastic members are fastened to the outside of the impervious enclosure.

As illustrated in FIGS. 1 and 2, the diaper according to the invention comprises a liquid-impervious outer enclosure 1, made from a flexible thin sheet, for example of polyethylene. The enclosure 1 comprises a rear transverse part 2, a front transverse part 3, which is advantageously of the same width as the transverse part 2 although a different width can be envisaged, and a central part 4 of smaller width, obtained by a lateral cutting-out of an indentation 5 at the location of the leg passages when the diaper is in use. The central part 4 of the crotch region is delimited in the example illustrated by a substantially rectilinear edge 6 parallel to the lengthwise axis of the diaper.

Fine lines of adhesive bonding 7, parallel to each other, have been applied continuously over the whole inner surface of the impervious enclosure 1. This operation, carried out continuously on the thin polyethylene sheet intended to form the enclosure is, of course, carried out before the cutting-out of the lateral indentations 5. Two elastic members 8 arranged rectilinearly in parallel to the lengthwise axis of the diaper have been coated with adhesives along their median part 9 between two lines of adhesive bonding 7, this operation being performed in the stretched state of the elastic members 8. The front and rear end parts 10 of the elastic members 8, on the other hand, are devoid of any adhesive so that, when the final transverse cutting of the complete continuous strip intended to form the individual diapers, these end parts retract, allowing the unstretched free ends which can be seen in FIG. 1 to appear. In the example illustrated in FIGS. 1 and 2, each of the elastic members 8 consists of a small band of a substantially rectangular cross-section made, for example, of rubber. It will obviously be understood that other materials could be employed and that the crossection of the elastic member could be easily modified, the essential being the fastening of the median part of the elastic member in the stretched state onto the impervious enclosure 1. In the same way, in the example illustrated, provision has been made for fitting the elastic members at a constant tension, the end parts 10 not being coated with adhesive. On the other hand, it would be perfectly possible to envisage coating the elastic members 8 continuously with adhesive while varying the tension at the time of fitting so that the front and rear ends of the elastic members 8 should be fitted without tension onto the impervious enclosure 1.

In the same way, while elastic members fitted along a continuous and rectilinear line have been illustrated here, it would be possible to envisage, in other embodiments, the use of elastic members fitted in parts, non-continuous or along a curved line, for example along the substantially curved outline of the lateral indentations 5.

An absorbent pad 11 is placed inside the impervious enclosure 1, being fastened to the latter by the multiple lengthwise lines of adhesive 7. As can be seen in FIG. 1, the absorbent pad is fastened set back in relation to the outermost edges of the impervious enclosure 1 so as to leave a lateral border 12 of the median part 4 of the impervious enclosure 1, remaining on each side of the pad, the elastic members 8 being arranged on this lateral border 12. In the example illustrated, the absorbent pad 11 has the general shape of an hour glass with a rear transverse part 13, a front transverse part 14 and a median part 15 of smaller width. The elastic members 8 are preferably coated with adhesive in their median part 9 as far as the vicinity of the edge of the absorbent pad 11 in its curvilinear part, which joins the median part 15 and the transverse parts 13 and 14. The absorbent pad 11 preferably consists of defibre cellulose pulp which is highly absorbent in nature. In a preferred embodiment a superabsorbent synthetic material consisting of water-insoluble polymers forming a gel, such as hydrocolloids capable of absorbing large quantities of liquids and of retaining the liquids thus absorbed, can also be adjoined to the absorbent material thus defined. For example, polymers of unsaturated carboxylic acids such as acrylic acid will be employed, these polymers being made water-insoluble by partial cross-linking of the carboxylic groups with cross-linking agents of a conventional type. Reference may be made, for example, to U.S. Pat. No. 4,654,039 (Brandt) which mentions many examples of such polymers of the prior art. This superabsorbent material may be uniformly distributed in the form of particles or of grains inside the absorbent pad or else may be distributed using layering between the separate layers of the absorbent pad 11.

Two bands 16 of thin flexible sheet, for example of polyethylene, are fastened, furthermore, by lines of adhesive bonding 7 or other lines of adhesive bonding which are closer together, on the inner face of the impervious enclosure 1 after the elastic members 8 have been fitted. The bands 16, fitted parallel to the lengthwise axis of the diaper, over its whole length, above each of the elastic members 8 define a kind of insulating sheath or tunnel which encloses the elastic member 8 over the whole length of the impervious enclosure 1. During the final transverse cutting defining the diapers, the ends 10 of the elastic members 8 undergo a retraction which has been referred to earlier, inside the insulating sheath thus defined, it being possible for the parts of elastic which are not adhesive-coated to slide freely inside this sheath.

As can be seen from the figures, the absorbent pad 11 is partly fitted on the bands 16, in particular in the region of the transverse ends 13 and 14. The bands 16 may also be arranged under the absorbent pad in its median region 15, although this arrangement is not critical. The essential, in fact, lies in the insulation of the sheath consisting of the band 16, this insulation being produced by the lengthwise lines of adhesive 7 which are responsible for the fastening of the bands 16 onto the inner face of the impervious enclosure 1. By virtue of this insulation, the tunnels or sheaths thus formed as a passage for the elastic members 8, in particular in the region of their front and rear ends 10, can no longer result in the outward escape of the liquids by draining of the urine absorbed by the pad. Similarly, any outward escape of the material of which the absorbent pad is made is avoided, especially in the case where the absorbent pad 11 comprises grains or particles of superabsorbent which may separate from the defibred cellulose pulp.

The bands 16 may be made of any suitable material, for example a nonwoven, based on cellulose fibres, optionally including plastic fibres such as polypropylene and the like. In the example illustrated in FIGS. 1 and 2, where the bands 16 are fastened by adhesive bonding onto the inner face of the impervious enclosure 1, the bands 16 are preferably made of an impervious material such as, for example, polyethylene, whose thickness may be approximately equal to that of the outer enclosure 1 so as to ensure a comparable flexibility.

The inner surface of the diaper is completely covered over with an inner permeable sheet 17 arranged on the inner face of the outer enclosure 1 and fastened by lengthwise lines of adhesive 7 all around the absorbent pad 11. The permeable sheet 17 thus at the same time covers the border parts of the impervious sheet 1, parts of the bands 16 and the whole of the absorbent pad 11. The permeable sheet 17 may be advantageously made of a voile of permeable nonwoven based on cellulose fibres or additionally containing fibres of synthetic material such as polyester, optionally mixed with nylon or polypropylene.

In the rear transverse part 2 the diaper also comprises two adhesive fastening devices 18 of a conventional type, enabling the diaper to be kept closed on the user.

The lengthwise lateral regions of the permeable sheet 17 are covered on their outer face, directed towards the impervious sheet 1 with a coating 19 of a sealing material. Such a material, called a "hot melt" in the usual technique, is liquid at a high temperature of the order of 100° C. and, after cooling, forms a nonadherent layer, substantially impervious to liquids. This layer coated on in this manner partly enters the actual thickness of the permeable sheet 17, as has been shown in a highly diagrammatic and exaggerated manner in FIG. 2 and without, however, passing completely through the sheet 17, which retains its soft feel for contact with the user's skin. The lateral coating 19 forms a barrier against the propagation of liquids. The urine which has entered the absorbent pad 11 can therefore no longer migrate outwards through the lateral parts of the permeable voile 17. In FIG. 1, the coating 19 outside the sheet 17 has been shown diagrammatically using broken lines. In actual fact, of course, the coating 19 cannot be seen from the inside. It should be noted that it is also possible to envisage placing the coating 19 towards the inside, on condition that a coating material which is not adhesive when cold is chosen.

The lateral coatings 19 are produced over the whole length of the diaper so as to form not only a barrier against the lateral migration of the liquid but also to produce, to some extent, a seal at the end of the insulating sheaths providing a passage for the elastic members 8. To this end, it is understood that the coating 19 is made over the region which comprises the bands 16, while the latter's presence prevents any entry of the coated sealing material inside the insulating sheaths. In these conditions, the sealing coating becomes possible despite the existence of the end parts 10 of the elastic members 8. Until now, in fact, it had not been possible to produce such lateral sealing by layers in practice by "hot melt" coating in diapers comprising elastic members at the leg passages because of the difficulties encountered in keeping the ends of the elastics free. By virtue of the present invention, the elastic members 8 are completely insulated by the bands 16 which extend over the whole length of the 1 diaper and it becomes possible to coat the lateral parts of the permeable sheet 17 over the whole length of the diaper, thus providing an excellent lateral barrier against the propagation of liquids.

The lateral coating 19 preferably applied as far as the parts of the permeable sheet 17 which overlap the lateral edges of the absorbent pad 11 so as to create, in a way, above the said absorbent pad, a permeable lengthwise strip delimited by two impervious borders consisting of the coatings 19. In the embodiment illustrated, the coatings 19 have been made as far as the outermost lateral edge of the diaper. It would be possible, however, to envisage limiting the coating to a lengthwise strip covering substantially the region of the bands 16 over the whole length of the diaper.

By way of examples of a sealing material which is liquid at high temperature and which may be employed in the present invention, there may be mentioned, the hot melt reference 5092-3-1 marketed by the National Adhesives and Resins Company, applied at approximately 135° C.; hot melt reference 8698-336, marketed by the Findley Company applied at approximately 135° C. and the hot melt reference 2-2271, marketed by the Malcolm Nicol Company, applied at approximately 145° C.

The coating of the sealing material which is liquid at high temperature ("hot melt") may be produced by means of any suitable device. A coating device using a die capable of depositing the liquid sealing material onto the strip of material travelling continuously and intended to form the diapers after transverse cutting will preferably be employed. By way of example, the devices sold by the Acumeter Laboratories Company may be employed. It is also possible to use a hot-melt applicator roll or spraying nozzles.

FIG. 3 illustrates an embodiment similar to the preceding embodiment with identical components bearing the same references. In this embodiment, however, the elastic members 8 have been replaced by a group of four individual elastic strands 20 arranged parallel to each other and coated with adhesive as previously in their median part. Each of the elastic strands 20 is substantially circular in cross-section. The band 16 which covers the set of the elastic strands 20 is responsible, as previously, for forming an insulating sheath for the elastic members. The individual elastic strands may be made of latex or of any other suitable elastic material.

In the embodiment in FIG. 4, where the identical components bear the same references, four individual elastic strands 20 have been arranged, no longer on the inner face of the impervious sheet 1, but on its outer face, substantially in the same general position as in FIG. 3. The bands 16 are then also fastened by adhesive bonding onto the outer face of the impervious enclosure 1 and over its whole length, forming, as previously, with the impervious enclosure 1, an insulating sheath which receives the elastic strands 20. It will be noted that the result obtained is the same as in the preceding embodiments, the liquids being unable to escape by any one of the tunnels formed by the passage for the elastic members, since the latter are bonded onto the outer face of the impervious enclosure 1.

As previously, the coating 19 cannot interfere with the retraction of the plastic members 20 during the transverse cutting of the diapers, by virtue of the interposition of the impervious enclosure 1.

In this embodiment, it is not necessary to employ an impervious material for the bands 16, and only the surface qualities of the material employed will be taken into account.

We claim:

1. In a disposable diaper for children or incontinent adults, comprising:
   a liquid impervious backsheet having outer lateral edges, an absorbent pad secured to the inner face of the impervious backsheet and having lateral edges mounted so as to leave a lateral border portion of said backsheet substantially free of absorbent material remaining on each side of the pad;
   an internal permeable sheet affixed to said backsheet and overlapping the inner face of the impervious backsheet and the absorbent pad;
   at least one lateral elastic member secured by adhesive bonding in a stretched state at least in the crotch area of each lateral border portion of the impervious backsheet, each elastic member having two end portions not secured to said backsheet and retracted between said backsheet and said internal sheet;
   the combination of two bands of flexible sheet, each defining an insulating sheath extending over the whole length of the impervious backsheet and having open ends secured to the impervious backsheet so that each sheath encloses a lateral elastic member with its two retracted end portions; and
   a hot melt coating forming a barrier against the propagation of liquids within the thickness of the said permeable sheet, said coating being applied on the face of said permeable sheet opposed to said absorbent pad, and longitudinally at least on the areas of the permeable sheet which overlap said two bands of flexible sheet, the lateral border portions of the backsheet and the lateral edges of the absorbent pad and over the whole length of the diaper, whereby the hot melt coating cannot enter into contact with the lateral elastic members enclosed in said insulating sheath.

2. Disposable diaper according to claim 1, characterized in that the coating (19) extends as far as the outermost lateral edges of the diaper.

3. Disposable diaper according to claim 1, characterized in that the bands (16) of the insulating sheaths are fastened onto the inner face of the impervious enclosure (1) and enclose the elastic members (8, 20) which are also fastened by adhesive bonding onto the inner face of the impervious enclosure (1).

4. Disposable diaper according to claim 3, characterized in that the bands (16) are made of liquid-impervious sheet.

5. Disposable diaper according to claim 1, characterized in that the bands (16) of the insulating sheaths are fastened onto the outer face of the impervious enclosure (1) and enclose the elastic members which are also fastened by adhesive bonding onto the outer face of the impervious enclosure (1).

6. Disposable diaper according to claim 1, characterized in that each of the elastic members consists of a small band of elastic material.

7. Disposable diaper according to claim 1, characterized in that each of the elastic members consists of a plurality of individual strands placed parallel to each other.

8. Disposable diaper according to claim 1, characterized in that the elastic members are fastened in the stretched state by adhesive coating in their median part, their front and rear ends which are not fastened being without tension and retracted inside the abovementioned insulating sheaths.

9. Disposable diaper according to claim 1, characterized in that the elastic members are rectilinear.

10. Disposable diaper according to claim 1 characterized in that the absorbent pad comprises defibred cellulose and grains of superabsorbent synthetic material.

11. Disposable diaper according to claim 2, characterized in that the bands of the insulating sheaths are fastened onto the inner face of the impervious enclosure and enclose the elastic members which are also fastened by adhesive bonding onto the inner face of the impervious enclosure.

12. Disposable diaper according to claim 2, characterized in that the bands of the insulating sheaths are fastened onto the outer face of the impervious enclosure and enclose the elastic members which are also fastened by adhesive bonding onto the outer face of the impervious enclosure.

13. Disposable diaper according to claim 2, characterized in that each of the elastic members consists of a small band of elastic material.

14. Disposable diaper according to claim 5, characterized in that each of the elastic members consists of a small band of elastic material.

15. Disposable diaper according to claim 5, characterized in that each of the elastic members consists of a plurality of individual strands placed parallel to each other.

16. Disposable diaper according to claim 7, characterized in that the elastic members are fastened in the stretched state by adhesive coating in their median part, their front and rear ends which are not fastened being without tension and retracted inside the above mentioned insulating sheaths.

17. Disposable diaper according to claim 8, characterized in that the elastic members are rectilinear.

18. Disposable diaper according to claim 9, characterized in that the absorbent pad comprises defibered cellulose and grains of superabsorbent synthetic material.

* * * * *